United States Patent
Gougel et al.

(10) Patent No.: US 7,462,749 B2
(45) Date of Patent: Dec. 9, 2008

(54) PROCESS FOR THE EXTRACTION OF ETHANOL FROM A WATER SOLUTION

(75) Inventors: Michail Gougel, Vårby (SE); Giuliano Grassi, Florence (IT)

(73) Assignee: Globelive International AB (SE)

( * ) Notice: Subject to any disclaimer, the term of this patent is extended or adjusted under 35 U.S.C. 154(b) by 0 days.

(21) Appl. No.: 10/599,308

(22) PCT Filed: Mar. 23, 2005

(86) PCT No.: PCT/SE2005/000425

§ 371 (c)(1),
(2), (4) Date: Sep. 25, 2006

(87) PCT Pub. No.: WO2005/092466

PCT Pub. Date: Oct. 6, 2005

(65) Prior Publication Data

US 2007/0205093 A1 Sep. 6, 2007

(30) Foreign Application Priority Data

Mar. 25, 2004 (SE) .................................. 0400775

(51) Int. Cl.
*C07C 29/76* (2006.01)
*C07C 29/74* (2006.01)

(52) U.S. Cl. .................................................... 568/917

(58) Field of Classification Search ................. 568/917
See application file for complete search history.

(56) References Cited

U.S. PATENT DOCUMENTS

| 4,492,637 | A | 1/1985 | Tao et al. |
| 4,874,524 | A | 10/1989 | Liapis et al. |
| 5,421,860 | A | 6/1995 | Bretz et al. |
| 5,427,689 | A | 6/1995 | Kallenbach et al. |

FOREIGN PATENT DOCUMENTS

| DE | 274 362 A1 | 12/1989 |
| WO | WO 0134267 A1 | 5/2001 |

OTHER PUBLICATIONS

International Search Report PCT/SE2005/000425 dated Jun. 22, 2005.
International Preliminary Examination Report dated Sep. 26, 2006.

*Primary Examiner*—Elvis O Price
(74) *Attorney, Agent, or Firm*—Ostrolenk, Faber, Gerb & Soffen, LLP

(57) ABSTRACT

A process for the extraction of ethanol from a solution by bringing the solution into contact with a bed of salt consisting of $Mg_3(PO_4)_2$, whereby the salt adsorbs ethanol from the solution, removing the solution from the salt bed, heating of the salt bed in order to release the ethanol adsorbed thereby as vapor and collecting the ethanol vapor. The use of particles of the salt for adsorption of ethanol from a solution.

5 Claims, 1 Drawing Sheet

PROCESS FOR THE EXTRACTION OF ETHANOL FROM A WATER SOLUTION

CROSS REFERENCE TO RELATED APPLICATION

The present application is a 35 U.S.C. §§ 371 national phase conversion of PCT/SE2005/000425, filed 23 Mar. 2005, which claims priority of Swedish Patent Application No.0400775-3 filed 25 Mar. 2004, which is herein incorporated by reference. The PCT International Application was published in the English language.

BACKGROUND OF THE INVENTION

The invention refers to a process for extraction of an ethanol from a solution thereof, according to the preamble of appended claim 1.

The separation of ethanol from a low-grade ethyl-alcohol solution is attractive for several reasons. First, the ethanol, for example bio-ethanol, can to advantage be produced by biochemical processes, such as fermentation of a mixture of water and sugars (or from starches or ligno-cellulosic feedstock). By fermentation of the mixture, a mash is produced, comprising i.a. a solution, having a relatively low concentration of ethyl-alcohol (in general 5%-12%). Usually, bio-ethanol is obtained by a fermentation of a C-6 sugar/water solution having a low concentration (10-25%). By extracting high-grade alcohol from the low-grade solution, a useful product is obtained, which can be used i.a. as fuel. Moreover, the liquid mixture or solution from which the ethanol is extracted sometimes represents a co-product, the usefulness and market value of which is improved by said extraction of alcohol.

One problem is however the costs for the extraction of high-grade ethanol from such low-grade solutions.

Another problem is that one or more properties of the liquid, from which the ethanol is extracted, are affected in a negative sense, by usual present extraction processes, in which the liquid is heated and alcohol is extracted by distillation up to, e.g. 96% (azeotropic bio-ethanol). Further processing to produce net bio-ethanol 100% can be performed by the use of molecular sieves.

SUMMARY OF THE INVENTION

One object of the invention is therefore to provide a process by which the energy consumption for the extraction of an ethanol from a solution is improved. A further object is to produce high-grade ethanol, in particular bio-ethanol from a low-grade solution by a one-step process. A further object is to provide a process in which the solution from which the ethanol is extracted does not have to be heated. The objects are, at least to some degree, reached by the invention.

The invention is defined in the appended independent claims.

Embodiments of the invention are defined in the appended depending claims.

An important feature of the invention is that the initial low-grade solution (mash) is brought into contact with a particle bed of a specific salt, namely $Mg_3(PO_4)_2$.

It has now surprisingly been found that $Mg_3(PO_4)_2$ chemically binds ethanol molecules from a solution. Since the salt chemically binds practically only ethanol, even from a low-grade alcohol solution, the ethanol vapour subsequently driven off from the bed will be high-grade. The ethanol vapour driven off from the salt bed is then collected and preferably condensed into liquid form.

The energy required to produce the ethanol is relatively small, since only the salt bed with the adsorbed ethanol has to be heated (not all of the solution) to release the ethanol, chemically bound ("adsorbed") in the salt.

The valuable product of the process can be the high-grade ethanol and/or solution from which the ethanol has been adsorbed. The removal of ethanol from the solution can sometimes be considered as a product improvement, especially since the solution is not heated by the process, so that the remaining content of the solution is not damaged by heating.

The solution could consist of a mash, which after adsorption of ethanol can be processed to obtain a useful animal feed product.

The salt bed can be kept under partial vacuum in order to reduce further the heating necessary to evaporate the ethanol.

One embodiment of the invention will now be described with reference to an extraction device.

DESCRIPTION OF A PREFERRED EMBODIMENT

Figure 1:
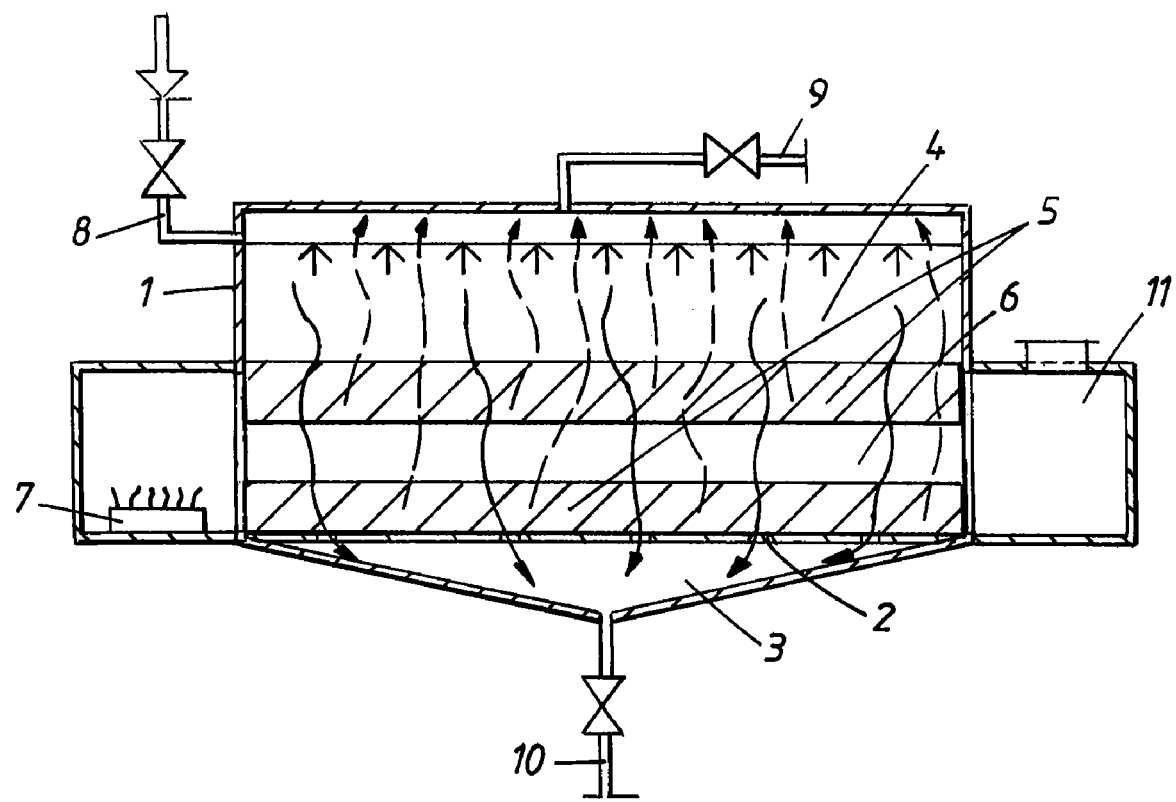
FIG. 1 illustrates schematically the construction of a device for performing the inventive process.

The device according to FIG. 1 is comprised of a closed vessel 1, provided with a perforated partition wall 2 that divides the vessel vertically into two parts, a bottom part 3 and a top part 4. Disposed in the top part 4 of the vessel, above the perforated partition wall 2 are heatable elements 6 and a layer or bed of salt 5, that will preferentially adsorb ethanol from a low-grade solution. The salt bed is in direct contact with the heatable elements 6. The elements 6 are heated by some energy source 7. For example, the energy source 7 could be a burner from which a flue gas is passed through elements 6 in the form of pipes which extend to a controllable valve device 11 for controlling the gas flow through the pipes 6, in order to control the heat supply through the pipes 6. Heat from the source 7 is delivered into the bed 5 through the pipe wall.

A liquid portion of the mash is delivered to the vessel 1 through a closable pipe 8, and a closable pipe 9 is provided for carrying away ethanol vapour, said pipes being placed in the upper part 4 of the vessel, above the salt bed 5. The salt bed 5 comprises a layer of salt granules. A pipe 10 is provided for carrying away the mash from which ethanol has been adsorbed by the salt and that has been collected in the lower part 3 of the vessel.

The device operates in the following way. The mash liquid is delivered to the pipe 8 connected to the upper part 4 of the vessel. The mash fluid passes through the bed of salt. The salt preferentially adsorbs ethanol from the mash liquid. The remainder of the mash delivered to the vessel, said mash now having a lower alcohol concentration is drained off from the salt bed and is carried away from the bottom part 3 of the vessel through the pipe 10. The mash liquid can be contacted with the salt bed to such an amount that essentially all of the ethanol content thereof is adsorbed by the salt bed, whereby the mash liquid drained off from the salt bed has an essentially ethyl-alcohol content of 0%. The ethanol content of a flow of mash liquid that leaves the apparatus after having passed through the salt bed, can be sensed. As soon as the ethanol content sensed raises significantly above 0%, the ethanol adsorption capacity of the bed can be considered exhausted. Then the input of mash liquid is stopped. The heat is delivered from a heat source 7 to the heatable element 6, whereby the salt of the salt bed 5 emits the adsorbed ethanol. If the heat source is a burner or the like, the flue gas flow can be controlled by the valve device 11. The ethanol alcohol is evacuated through the pipe 9. This ethanol vapour is converted, by cooling, into a condensate. The high-grade alcohol thus formed can be used as a fuel, for example.

On advantage of the invention is that only the salt bed with adsorbed ethanol has to be heated (not all of the mash liquid), and a further advantage is that the heating process performed to drive off the ethanol adsorbed by the salt also regenerates the salt for a new cycle. Trials have shown that the salt should have a solubility product of not higher than $10^{-24}$, since otherwise the salt dissolution and the need to add new salt crystals to the bed will be disturbing $Mg_3(PO_4)_2$ is the preferred salt used in the present invention, has such a solubility product.

The heatable elements can be heated by energy from conventional sources or preferably from renewable energy in particular bioenergy for example, by fuel pellets which preferably are made from renewable biological material, for example agro-forestry residues.

In the drawing, the mash liquid flow is indicated with full arrows, while the vapour flow is indicated with broken arrows in the drawing.

The device shown on the drawing constitutes a system for batch operation. However, it is obvious that two such devices could be connected in parallel and driven in sequence in opposite phases in order to provide a continuous production of alcohol.

The invention claimed is:

1. A process for the extraction of ethanol from a solution, characterized by bringing the solution into contact with a bed of a salt Mg3(PO4)2, whereby the salt adsorbs ethanol from the solution, removing the solution from the salt bed, heating of the salt bed in order to release the ethanol adsorbed thereby as vapor and collecting the ethanol.

2. A process according to claim 1, wherein the salt preferentially adsorbs ethanol molecules from a low-grade ethyl-alcohol solution, whereby high-grade ethanol can be obtained from the low concentration alcohol solution, in a one-step process.

3. A process according to claim 1, wherein the solution consists of a low-grade ethyl-alcohol liquid which has been separated from a mash.

4. A process according to claim 1, wherein by passing a flow of the solution through the bed, sensing the ethyl-alcohol content of the solution leaving the bed, and stopping the input flow to the bed when the sensed alcohol content of the solution leaving the bed significantly raises above 0%, and collecting the solution leaving the bed and having an alcohol content of about 0%.

5. A process according to claim 1, wherein the salt preferentially adsorbs ethanol molecules from a low-grade ethyl-alcohol solution, whereby high-grade ethanol can be obtained from the low concentration alcohol solution, in a one-step process.

* * * * *